(12) United States Patent
Aberg et al.

(10) Patent No.: US 9,138,431 B2
(45) Date of Patent: Sep. 22, 2015

(54) METHODS OF TREATMENT OF HISTAMINE H-4 RECEPTOR-RELATED PRURITUS

(71) Applicant: BRIDGE PHARMA, INC., Sarasota, FL (US)

(72) Inventors: A. K. Gunnar Aberg, Sarasota, FL (US); Vincent B. Ciofalo, Branford, CT (US)

(73) Assignee: BRIDGE PHARMA, INC., Sarasota, FL (US)

( * ) Notice: Subject to any disclaimer, the term of this patent is extended or adjusted under 35 U.S.C. 154(b) by 0 days.

(21) Appl. No.: 13/960,114

(22) Filed: Aug. 6, 2013

(65) Prior Publication Data

US 2015/0045392 A1 Feb. 12, 2015

(51) Int. Cl.
*A01N 43/40* (2006.01)
*A61K 31/445* (2006.01)
*A61K 31/4535* (2006.01)

(52) U.S. Cl.
CPC ................................. *A61K 31/4535* (2013.01)

(58) Field of Classification Search
None
See application file for complete search history.

(56) References Cited

U.S. PATENT DOCUMENTS

| | | | |
|---|---|---|---|
| 3,682,930 A | 8/1972 | Bourquin et al. | |
| 4,659,716 A | 4/1987 | Villani et al. | |
| 5,595,997 A | 1/1997 | Aberg et al. | |
| 6,207,683 B1 | 3/2001 | Aberg et al. | |
| 6,207,684 B1 | 3/2001 | Aberg | |
| 7,226,934 B1 * | 6/2007 | Aberg et al. | 514/324 |
| 7,557,128 B2 | 7/2009 | Aberg et al. | |
| 8,557,846 B1 | 10/2013 | Aberg et al. | |
| 2010/0105734 A1 | 4/2010 | Aberg et al. | |
| 2010/0130550 A1 | 5/2010 | Aberg et al. | |
| 2010/0160271 A1 * | 6/2010 | Gant | 514/171 |
| 2010/0249202 A1 | 9/2010 | Koga et al. | |

FOREIGN PATENT DOCUMENTS

| | | |
|---|---|---|
| WO | 0119367 A1 | 3/2001 |
| WO | 03057919 A2 | 7/2003 |
| WO | 2008153761 A1 | 12/2008 |
| WO | 2009142772 A2 | 11/2009 |
| WO | 2014066212 A1 | 5/2014 |

OTHER PUBLICATIONS

Katagiri et al. (Journal of Dermatology, 2006, 2, 75-79).*
Eczema Health Center, WebMD, May 14, 2012.*
Wheeler, Everyday Health, "Antihistamines Take the Itch Out of Eczema", Sep. 23, 2013, http://www.everydayhealth.com/eczema/antihistamines-take-the-itch-out-of-eczema.aspx.*
U.S. Appl. No. 13/744,807, filed Jan. 18, 2013; Final Office Action, Mailed Aug. 2, 2013; 23 pages.
Varsano et al; "Multicenter Study with Ketotifen (Zaditen) Oral Drop Solution in the Treatment of Wheezy Children Aged 6 Months to 3 Years"; Pediatr Allergy Immunol; 4(1); pp. 45-50; (1993) Abstract Only.
DeBoer et al.; "The ACVD Task Force on Canine Atopic Dermatitis (XII): The Relationship of Cutaneous Infections to the Pathogenesis and Clinical Course of Canine Atopic Dermatitis"; Vererinary Immunology and Immunopathology; 81; pp. 239-249; (2001).
Murota et al.; "Impact of Sedative and Non-Sedative Antihistamines on the Impaired Productivity and Quality of Life in Patients with Pruritic Skin Diseases"; Allergology International; 59; pp. 345-354; (2010).
Uto, C.; "Histamine H3-receptor Inverse Agonists as Novel Antipsychotics"; Cent Nery Syst Agents Md Chem.; PubMed—NCBI; 2009; abstract only; printed Dec. 14, 2012; 1 page.
U.S. Appl. No. 10/069,663, filed Nov. 29, 2006; 1.132 Declaration of A.K. Gunnar Aberg, filed Dec. 14, 2006; 3 pages.
U.S. Appl. No. 13/739,090, filed Jan. 11, 2013; A.K. Gunnar Abert; Medicinal Treatment of Dermal Diseases in Dogs; copy of which may be found in the Image File Wrapper.
U.S. Appl. No. 13/739,090, filed Jan. 11, 2013 NonFinal Office Action Mailed May 3, 2013; a copy of which may be found in the image file wrapper.
U.S. Appl. No. 13/744,807, filed Jan. 18, 2013; A.K. Gunnar Abert and Vincent B. Ciofalo; Medicinal Treatment of Atopic Inflammatory Diseases; copy of which may be found in the Image File Wrapper.
U.S. Appl. No. 13/744,807, filed Jan. 18, 2013; NonFinal Office Action; Mailed Jun. 7, 2013; 43 pages; Copy of which may be found in the Image File Wrapper.
Zampeli et al.; "The Role of Histamine H4 Receptor in Immune and Inflammatory Disorders"; Abstract; British Journal of Pharmacol.; 157(1); pp. 24-33; (2009).
Baumer; "Sphingosine-1-phosphate and Histamine H4 Receptors as New Therapeutic Targets for Allergic Skin Diseases"; pp. 38-40; from Keynote Lectures; J. Vet. Pharmacol. Therap.; 32(Suppl. 1), pp. 11-46; (2009).
Bell et al.; Involvement of Histamine H4 and H1 Receptors in Scratching Induced by Histamine Receptor Agonists in BalbC Mice; J Pharmacol.; 142(2); p. 374-380; (2004).
Cheng et al.; "Relationship Between the Inhibition Constant (K1) and the Concentration of Inhibitor Which Causes 50 Per Cent Inhibition (I50) of an Enzymatic Reaction"; Biochemical Pharmacology; 22; pp. 3099-3108; (1973).
Cowden, et al.; "The Histamine H4 Receptor Mediates Inflammation and Pruritus in Th2-Dependent Dermal Inflammation"; Journal of Investigative Dermatology; 130; pp. 1023-1033; (2010).

(Continued)

*Primary Examiner* — Dennis Heyer
*Assistant Examiner* — Daniel M Podgorski
(74) *Attorney, Agent, or Firm* — Cantor Colburn LLP

(57) ABSTRACT

The methods disclosed herein relate to the treatment of histamine H-4—related pruritus, by administering a histamine H-4 receptor inverse agonist that selectively accumulates at the biophases of the disorders, specifically RS-norketotifen or a pharmaceutically acceptable salt thereof. Potentiated antipruritic activity by simultaneous inhibition of histamine H-1 receptors and histamine H-4 receptors are described.

6 Claims, 1 Drawing Sheet

(56) References Cited

OTHER PUBLICATIONS

Deml et al.; "Interactions of Histamine H1-Receptor Agonists and Antagonists with the Human Histamine H4-Receptor"; Molecular Pharmacology; 76; pp. 1019-1030; (2009).
"Dog Skin Disorders" by Wikipedia; 2 pages; http://en.wikipedia.org/wiki/Dog_skin_disorders; printed Oct. 15, 2012.
Dunford et al; "Histamine H4 Receptor Antagonists are Superior to Traditional Antihistamines in the Attenuation of Experimental Pruritus"; J. Allergy Clin Immunol; 119(1); pp. 176-183; (2006).
Gantner et al.; "Histamine H4 and H2 Receptors Control Histamine-Induced Interleukin-16 Release from Human CD8+ T Cells"; The Journal of Pharmacology and Experimental Therapeutics; 303; pp. 300-307; (2002).
Gschwandtner et al.; "The Histamine H4 Receptor Is Highly Expressed on Plasmacytoid Dendritic Cells in Psoriasis and Histamine Regulates Their Cytokine Production and Migration"; Journal of Investigative Dermatology; 131; pp. 1668-1676; (2011).
Guidance for Industry; "Estimating the Maximum Safe Starting Dose in Initial Clinical Trials for Therapeutics in Adult Healthy Volunteers"; U.S. Department of Health and Human Services Food and Drug Administration Center for Drug Evaluation and Research; Jul. 2005; 26 pages.
Gutzmer et al.; "Pathogenetic and Therapeutic Implications of the Histamine H4 Receptor in Inflammatory Skin Diseases and Pruritus"; Frontiers in Bioscience; S3; pp. 985-994; (2011).
Hiller et al.; "The ACVD Task Force on Canine Atopic Dermatitis (I): Incidence and Prevalence"; Veterinary Immunology and Immunopathology; 81; pp. 147-151; (2001).
Ito, C.; "Histamine H3-receptor Inverse Agonists as Novel Antipsychotics"; Cent Nery Syst Agents Md Chem.; PubMed—NCBI; 2009; abstract only; printed Dec. 14, 2012; 1 page.
Jiang et al.; "Cloning and Pharmacological Characterization of the Dog Histamine H4 Receptor"; European Journal of Pharmacology; 592; pp. 26-32; (2008).
Kennedy, G.R.; "Metabolism and Pharmacokinetics of Ketotifen in Children"; Research and Clinical Forums; 4; pp. 17-20; (1982).
Ketotifen (Systemic); Professional Drug Information, Drugs.com, updated Mar. 6, 2008, Mar. 17, 2008 and Mar. 12, 2008;, printed Jul. 13, 2013; 11 pages.
Le Bigot et al.; "Metabolism of Ketotifen by Human Liver Microsomes_In Vitro Characterization of a Tertiary Amine Glucuronidation"; Drug Metabolism and Disposition; 11(6); pp. 585-589; (1983).
Liu et al.; "Cloning and Pharmacological Characterization of a Fourth Histamine Receptor (H4) Expressed in Bone Marrow"; Molecular Pharmacology; 59; pp. 420-426; (2001).
Maclay et al.; "Postmarketing Surveillance: Practical Experience With Ketotifen"; British Medical Journal; 288; pp. 911-914 (1984).
Massari et al.; "Role of H4 Receptor in Histamine-Mediated Responses in Human Melanoma"; Melanoma Res.; 21 (5); pp. 395-404; (2011).
Matsushita, et al.; "Advantages of Histamine H4 Receptor antagonist Usage With H1 Receptor Antagonist for the Treatment of Murine Allergic Contact Dermatitis"; Experimental Dermatology; 21; pp. 710-720; (2012).
Mommert; et al.; "The Role of the Histamine H4 Receptor in Atopic Dermatitis"; Curr Allergy Asthma Rep; 11; pp. 21-28; (2011).
Nakamura, et al.; "Molecular Cloning and Characterization of a New Human Histamine Receptor, HH4R"; Biochem Biophy Res Commun.; PubMed—NCBI; 2000; printed Jun. 28, 2013; abstract only; 1 page.
Nakayama et al.; "Liver-Expressed Chemokine/CC Chemokine Ligand 16 Attracts Eosinophils by Interacting with Histamine H4 Receptor"; The Journal of Immunology; pp. 2078-2083; (2004).
Neilly et al.; "Pruritus in Diabetes Mellitus: Investigation of Prevalence and Correlation With Diabetees Control"; Diabetes Care; 9(3); pp. 273-275; (1986).
Nolte et al.; "Inhibition of Basophil Histamine Release by Methotrexate"; Abstract; Agents Actions; 23(3-4); pp. 173-176; (1988).

Dogs with Atopic Determatitis: Causes, Diagnosis, and Treatment; from WebMD http://pets.webmd.com/dogs/dogs-atopic-dermatitis-causes-diagnosis-treatment; 3 pages; printed Dec. 31, 2012.
"Zaditen"; Novartis, Pharmaceutical Information, Product monograph, printed Jul. 16, 2013; 3 pages.
Oaklander et al.; "Common Neuropathic Itch Syndromes"; Acta Derm Venereol; 92; pp. 118-135; (2012.
Oda et al.; "Molecular Cloning and Characterization of a Novel Type of Histamine Receptor Preferentially Expressed in Leukocytes"; Journal of Biological Chemistry; 275(47); pp. 36781-36786; (2000).
Potenzieri, et al.; "Basic mechanisms of Itch"; Clin Exp allergy; 42(1); pp. 8-19; (2012).
Prowse, Keith; "Ketotifen in Adult Asthma"; British Medical Journal; 280; p. 646; (1980).
Robbach et al.; "Histamine H4 Receptor Antagonism Reduces Hapten-induced Scratching Behaviour but Not Imflammation"; Experimental dermatology; 18; pp. 57-63; (2008).
Robbach et al.; "The Histamine H4 Receptor as a New Target for Treatment of Canine Inflammatory Skin Diseases"; Veterinary Dermatology; 20; pp. 555-561; (2009).
Roquet et al.; "Effects of Loratadine on Anti-IgE-Induced Inflammation, Histamine Release, and Leukocyte Recruitment in Skin of Atopics"; Allergy; 50(5); pp. 414-420; Abstract Only; (1995).
Ruben, Dawn; Diphenhydramine (Benadryl(R)); www.petplace.com/drug-library/diphenhydramine-benadryl/page1.aspx; 2 pages; printed Oct. 16, 2012.
Seike et al.; "Histaminen H4 Receptor Antagonist Ameliorates Chronic Allergic Contact Dermatitis Induced by Repeated Challenge"; Allergy; 65; pp. 319-326; (2010).
"U.S. Pet Ownership Statistocs"; by The Humane Society of the United States; www.humanesociety.org/issues/pet_overpopulation/facts/pet_ownership_statistics.html; 2 pages; printed Dec. 31, 2012.
Thomas, Randall C.; Proceeding of the North American Veterinary Conference, "Canine Atopic Dermatitis: Old and New Therapies"; pp. 285-288; (2005).
Thurmond et al.; "The Role of Histamine H1 and H4 Receptors in Allergic Inflammation: The Search for New Antihistamines"; Nature Reviews; 7; pp. 41-53; (2008).
Tonelli et al.; "A Bio-assay for the Concomitant Assessment of the Antiphlogistic and Thymolytic Activities of Topically Applied Corticoids"; Endocrinology; 77; pp. 625-634; (1964).
Waldvogel et al.; "Untersuchunger uber synthetische Arzneimittel 9- and 10-Oxo-Derivate von 9,10-Dihydro-4H-benzo[4,5]cyclohepta-[1,2-b} thiophenenSynthetical pharmaceutics. 9- and 10- Oxo derivatives of 9,10-dihydro-4H-benzo-[4,5]-cyclohepta[1,2b]thiophenes"; Helvetica Chimica Acta;; 59(3); pp. 866-877; (1976) with machine translated English Abstract.
Wauquier et al.; "Further Studies on the Distinctive Sleep-Wakefulness Profiles of Antihistamines (Astemizole, Ketotifen, Terfenadine) in Dogs"; Drug Development Research; 4; pp. 617-625; (1984).
Yamaura et al.; "Expression of the Histamine H4 Receptor in Human Tissue"; in Chapter 2. Allergic Diseases—Highlights in the Clinic, Mechanisms and Treatment; Celso Pereira, Ed.; pp. 31-42; (2012).
Narkus et al.; "The Placebo Effect in Allergen-specific Immunotherapy Trials"; Clinical and Translational Allergy; 3 (42) pp. 1-8; (2013).
Lane, D.J.; "A Steroid Sparing Effect of Ketotifen in Steroid-Dependent Asthmatics"; Clinical Allgergy; 10; pp. 519-525; (1980).
Polivka et al.; "4H-Benzol[4,5]Cyclohepta[1,2-b]Thiophenes and 9,10-Dihydro Derivatives—Sulfonium Analogues of Pzotifen and Ketotifen; Chirality of Ketotifen; Synthesis of the 2-Bromo Derivative of Ketotifen"; Collect. Czech. Chem. Commun.; (54); pp. 2443-2469; (1989).
International Search Report and Written Opinion; International Application No. PCT/US2014/049173; International Filing Date Jul. 31, 2014; Date of Mailing Sep. 24, 2014; 11 pages.
Tey et al.; "Targeted Treatment of Pruritus: a Look Into the Future"; BR J Dermatol; 165(1); 5-17 (2011) abstract.
Benadryl Allergy Ultratab Tablets; Product Description; www.benadryl.com; printed Oct. 2014; 2 pages.
Benadryl Itch Cream; Product Description; www.benadryl.com; printed Oct. 2014; 3 pages.

(56) References Cited

OTHER PUBLICATIONS

Yamaura et al.; "Expression of Histamine H4 Receptor in Human Epidermal Tissues and Attenuation of Experimental Pruritus Using H4 Receptor Antagonist"; Journal of Toxicological Sciences; 34(4); pp. 427-431; (2009).

Robbach et al.; "Histamine H4 Receptor Antagonism Reduces Hapten-induced Scratching Behaviour but Not Inflammation"; Experimental Dermatology; 18; pp. 47-63; (2008).

Akdis et al;"Diagnosis and Treatment of Atopic Dermatitis in Children and Adults:European Academy of Allergology and Clinical Immunology/American Academy of Allergy, Asthma and Immunology/Practall Consensus Report";J Allergy Clin Immunol;118(1);pp. 152-169; (2006).

Dunford et al.; Histamine H4 Receptor Antagonists are Superior to Traditional Antihistamines in the Attenuation of Experimental Pruritus;J Allergy Clin Immunol; 119(1);pp. 176-183; (2007).

Mommert et al.; "The Role of the Histamine H4 Receptor in Atopic Dermatitis"; Curr Allergy Asthma Rep; 11; pp. 21-28; (2011).

* cited by examiner

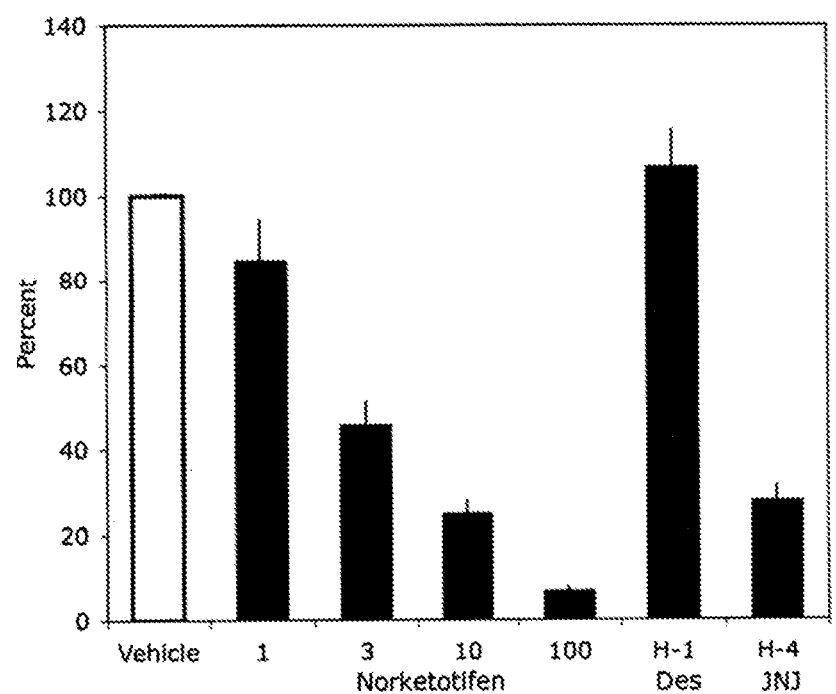

METHODS OF TREATMENT OF HISTAMINE H-4 RECEPTOR-RELATED PRURITUS

TECHNICAL FIELD

The embodiments disclosed herein relate to methods of norketotifen-treatment of medical conditions that are mediated through histamine H-4 receptors in mammals.

BACKGROUND

Four histamine receptors (H-1, H-2, H-3, H-4) have been identified, all of which are G protein-coupled receptors. The four different receptors are expressed on various cell types and exert their effects through different intracellular signaling mechanisms, which may in part be related to the diverse effects of histamine in different cells, tissues and organs.

The human histamine H-4 receptor is active constitutively, as is also the case with human histamine H-1, H-2 and H-3 receptors. Thus, like all other histamine receptor inhibitors, histamine H-4 receptor inhibitors are inverse agonists on the human histamine receptors.

Several potent and selective histamine H-4 receptor ligands have been described, such as for example JNJ 7777120, JNJ 10191584 and 4-methylhistamine. Such ligands will bind to all human histamine H-4 receptors, wherever those receptors are expressed in the body, such as for example, in bone marrow and white blood cells. The disadvantage of these compounds is that they act with high potency inhibiting histamine H-4 receptors throughout the body, increasing the likelihood of unwanted systemic side effects.

What is needed are improved methods of selectively treating medical conditions associated with histamine H-4 receptors at the biophases of those conditions.

SUMMARY

In one aspect, disclosed herein is a method of treating a mammal in need of treatment for histamine H-4 receptor-related pruritus, comprising orally administering to the mammal in need thereof a therapeutically effective amount of RS-norketotifen or a pharmaceutically acceptable salt thereof. In specific embodiments, administration of the therapeutically effective amount of norketotifen or a pharmaceutically acceptable salt thereof is expected to avoid systemic histamine-H-4-related adverse drug effects, because the orally administered amount of the drug accumulates in the skin, which is the largest organ in the body.

In another aspect, a method of treating a mammal in need of treatment for histamine H-4 receptor-related pruritus without inducing systemic side effects is described and comprises orally administering to the mammal in need thereof a therapeutically effective amount of a biophase-selective histamine H-4 receptor inhibitor, wherein the biophase-selective histamine H-4 receptor inhibitor is norketotifen, an isomer of norketotifen, or a pharmaceutically acceptable salt of racemic or isomeric norketotifen. Pruritus (itch) is a sensation that causes the desire or reflex to scratch. Pain and pruritus have anatomical and physiological similarities, but while pain evokes a withdrawal reflex, pruritus creates a scratching reflex. Often multiple scratches are evoked, usually called "bouts of scratches". The word "pruritus" is Latin for "itch".

BRIEF DESCRIPTION OF THE FIGURES

FIG. 1 shows the effects of test articles on histamine-induced pruritus in mice. (N=8, if not differently stated)

DETAILED DESCRIPTION

Histamine H-4 receptors are known to be expressed in the skin as well as in the pulmonary and gastrointestinal tissues of humans and of animals. Histamine H-4 receptors are also expressed in bone marrow, and serious side effects, such as for example, agranulocytosis, are believed to be related to the activity of potent histamine H-4 receptor inhibitors. Without being held to theory, it is believed that systemic adverse effects will be less pronounced for compounds that are selectively distributed to specific biophase organs or tissues where the compounds may accumulate in concentrations that are higher than the systemic plasma concentration. Such compounds will reach concentrations that inhibit histamine H-4 receptors locally in the specific organs or tissues, thereby reducing the systemic exposure and the incidence of systemic side effects. Thus, rather than increasing the potency or the dose of histamine H-4 receptor ligands, it may be advantageous to use a histamine H-4 receptor inhibitor that accumulates at the biophase(s) for diseases. Such compounds will selectively express histamine H-4 receptor inverse agonistic activity where they are accumulated, while avoiding the adverse effects of evenly distributed ligands with high affinity for the histamine H-4 receptors.

As used herein, the term biophase refers to the site(s) where a drug expresses its therapeutic activity. For example, if a receptor is associated with a disorder in the skin, then the biophase is the skin.

As used herein, a potent histamine H-4 receptor inverse agonist has a Ki less than 3.0E-7M, while moderately active compounds have Ki between 3.0E-6M and 3.0E-7M.

It is highly advantageous if compounds with moderate histamine H-4 receptor activity accumulate where they are anatomically therapeutically active; the moderate activity will not express systemic adverse effects, such as for example agranulocytosis. Such compounds are herein called biophase-selective histamine H-4 receptor ligands or biophase-selective histamine H-4 inhibitors or biophase-selective histamine H-4 inverse agonists.

It has specifically been found that after oral administration, racemic norketotifen (RS-norketotifen) and the isomers thereof (R-norketotifen, S-norketotifen) accumulate in the skin. The skin is the biophase for dermal diseases and the pharmacokinetic exposure parameters—area under the curve, half-lives and mean residence times—of norketotifen in this biophase have been found to significantly exceed the corresponding parameters in the systemic circulation (See, e.g., Example 4.) The high concentrations of these compounds in skin (See, e.g., Example 4) will inhibit the histaminic H-4 receptors (See, e.g., Examples 2 and 3), particularly since these compounds potently decrease the concentrations of available histamine at the biophase (See, e.g., Example 1). Thus, RS-, R- and S-norketotifen, as well as other histamine H-4 receptor inhibitors that are distributed in high concentrations in the skin, can advantageously be used to treat diseases or medical conditions associated with dermal histamine H-4 receptors.

Further, norketotifen and the isomers thereof have moderate affinity for histamine H-4 receptors. This moderate affinity combined with the localization in the biophases of the skin and lungs avoids adverse effects induced by systemically active histamine H-4 receptor inhibitors.

In one embodiment, disclosed herein is a method treating a mammal in need of treatment for histamine H-4 receptor-related pruritus, comprising orally administering to the mammal in need thereof a therapeutically effective amount of a biophase-specific H-4-receptor inhibitor. In specific embodiments, the biophase-selective histamine H-4 receptor inhibitors are RS-, R- or S-norketotifen, or pharmaceutically acceptable salts thereof, specifically RS-norketotifen or pharmaceutically acceptable salts thereof. In one aspect, the histamine H4-receptor-related disorder is not histamine H-1-related.

Exemplary histamine H-4 receptor-related dermal disorders include histamine H-4 receptor-related pruritic disorders. Activation of dermal histamine H-4 receptors by histamine or other endogenous H-4 receptor agonists, such as for example CCL16, results in pruritus that is caused by pruritic mechanisms that are regulated by histamine H-4 receptors.

In one aspect, a method of treating a mammal in need of treatment for histamine H-4 receptor-related pruritus comprises orally administering to the mammal in need thereof a therapeutically effective amount of a biophase-selective histamine H-4 receptor inhibitor, wherein the biophase-selective histamine H-4 receptor inhibitor is norketotifen, an isomer of norketotifen, or a pharmaceutically acceptable salt thereof. In one embodiment, the histamine H-4 receptor-related pruritus is resistant to treatment with histamine H-1 receptor inhibitors.

Pruritus (itching) is an unpleasant sensation that—contrary to pain—elicits the desire to scratch. Histamine H-4 receptor-related pruritus can be associated with various disorders and conditions, such as for example:

Adverse Effects of Prescription Drugs: antibiotics, antifungals, pain relievers;

Dermal Disorders: autoimmune dermatitis, contact dermatitis, dermal scleroderma, folliculitis, idiopathic dermatitis, infections, insect bites, melanoma, parasites, scabies, sunburn, warts, xerosis and dermal conditions such as moles, hyperpigmentation, hypopigmentation and rashes;

Systemic Disorders: anemia, cholestasis, diabetes, Hodgkin lymphoma, iron deficiency, chronic renal failure, systemic scleroderma, multiple sclerosis, uremia, and conditions such as pregnancy;

Nerve disorders: multiple sclerosis, neuropathic pruritus, scars, shingles;

Psychological disorders: anxiety, depression, emotional stress, neurodermatitis, psychological trauma, psychoses; and Idiopathic pruritus: various forms of pruritus, where the cause for the itching has not been successfully determined.

Scratching behavior is a sign of pruritus and can be studied in humans and in mice after intradermal injections of histamine. Pruritus following histamine injections is not inhibited by histamine H-1 inhibitors, such as desloratadine (Clarinex® Merck Sharp & Dohme), diphenhydramine (Benadryl® McNeil) or fexofenadine (Allegra® Sanofi Aventis). Histamine-induced pruritus is potently inhibited by histamine H-4 inhibitors, such as for example JNJ7777120 and norketotifen (Example 5).

The methods for treatment of pruritus, disclosed herein, are useful in the treatment of non-humans as well as humans. While it is well known that the human histamine H-4 receptor expresses constitutive activity, it is possible that non-human histamine H-4-receptors do not express constitutive activity. If it is confirmed that the canine and feline histamine H-4 receptor does not express constitutive activity and/or norketotifen therefore proves not to be an inverse histamine H-4 receptor agonist on the canine histamine H-4 receptor, the correct terminology herein shall be "antagonist" or "inhibitor" rather than "inverse agonist". Therefore, and to improve clarity with regard to histamine H-4 receptors, the terms antagonist, inhibitor and inverse agonist will herein be considered as homologs and will be alternatingly used. The human histamine H-4 receptor has a high homology with the canine histamine H-4 receptor, the homology being 71 percent.

Another advantage of the use of norketotifen and its isomers is that those compounds express inhibitory activities at both histamine H-1 receptors and histamine H-4 receptors. There is a benefit to inhibiting the activities of both H-1 and H-4 receptors, since co-administration of histamine H-1 and histamine H-4 receptor inhibitors can completely inhibit some pruritic effects, such as for example types of pruritus with high intradermal concentrations of histamine. It is believed that the histamine H-4-receptor mediated pruritic activity is initiated locally in the skin, where pruritogenic mediators activate receptors on neuronal C-fibers. However, the mechanisms for the potentiated antipruritic activities of histamine H-1 receptor inhibitors and histamine H-4 receptor inhibitors are presently not understood.

Despite the advantages of combinations of compounds that inhibit histamine H-1 receptors with compounds that inhibit H-4 receptors, no compound with a combination of histamine H-1 receptor and histamine H-4 receptor inhibitory activities has, to our knowledge, been described previously. Norketotifen and the isomers thereof have such combined activities.

Not all types of pruritus are inhibited by histamine H-4 receptor inhibition. Thus, for example, the selective histamine-4 receptor inhibitor JNJ7777120 failed to inhibit pruritus induced by interleukin-31 (IL-31) in a recent study.

Norketotifen can be made from methods known in the art, as described in U.S. Pat. No. 3,682,930, the disclosure of which is hereby incorporated by reference for its teaching of the synthesis of norketotifen.

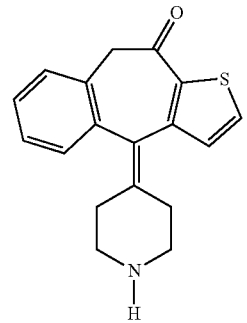

NORKETOTIFEN

The norketotifen isomers can be made as described in U.S. Pat. No. 7,226,934 and U.S. Pat. No. 7,557,128, the disclosures of which are hereby incorporated by reference for their teaching of the synthesis of norketotifen isomers.

Norketotifen is the active metabolite of ketotifen, which is a Generation-1 antihistamine. Ketotifen may be the most potent antihistamine ever marketed, but it is also the most sedating of all marketed antihistamines. The sedative effects of ketotifen are strictly dose-limiting and doses higher than 1 mg, bid are rarely used. It is currently believed that approximately 0.5 mg norketotifen is formed in the human body for every 1 mg of ketotifen that is administered. The metabolism—a demethylation of the piperidine nitrogen—takes place in the liver. The sedation by ketotifen is caused by ketotifen per se (the "prodrug") while the disease-modifying effects of the drug are believed to be due to the metabolite norketotifen. The currently used therapeutic doses of ketotifen—1 mg bid to humans—are not high enough to offer therapeutic activity by inhibition of histamine H-4 receptor activity. (See, e.g., Example 3, Table 3).

Repeat-dose pharmacological and toxicological studies have now been performed in dogs and it has surprisingly been found that daily doses up to 20 mg/kg/day of racemic or isomeric norketotifen can be given chronically to dogs without causing sedation or other adverse events. Doses up to 28 mg/kg/day did not cause sedation and were tolerated by the dogs, but single oral doses of norketotifen of 4 mg/kg to 20 mg/kg are preferred to obtain inhibition of H-4 receptors in the lungs and in the skin of dogs. Dogs vomit spontaneously for a variety of benign reasons—to expel unwanted content from their stomach, as a result of gastric irritation or in response to colonic irritation. In recent toxicological studies in dogs of various drugs, including isomeric norketotifen, vomiting occurred in both control groups and drug groups and may have been treatment-related, rather than drug-related. The unexpectedly low systemic toxicity of norketotifen and the isomers thereof is believed to be due to low systemic (plasma) concentrations, caused by the fact that norketotifen and the isomers thereof are not circulating in plasma but are accumulating in the skin, which is the largest organ in the body.

Similarly, it has been found that doses of 5 mg and 10 mg of norketotifen in humans also do not produce sedation when tested in human subjects.

It is presently estimated that inhibition of histamine H-4 receptor activity at the biophases in mammals suffering from histamine H-4 receptor-related dermal or pulmonary disorders, will occur at oral doses of norketotifen or an isomer thereof from approximately 2 mg/day to approximately 500 mg/day, which leaves a wide safety margin. Useful doses of racemic or isomeric norketotifen to human patients suffering from said disorders are between 2 mg/day and 500 mg/day. More preferred is a daily oral dose of 2 mg/day to 40 mg/day to a human patient and most preferred is a human dose of 2 mg/day to 20 mg/day of norketotifen or an isomers thereof to human patients suffering from histamine H-4 receptor-related dermal or pulmonary diseases.

Useful oral doses of racemic norketotifen or an isomer thereof are 2 mg/kg/day to 28 mg/kg/day to dogs suffering from pruritus diseases. More preferred are oral doses ranging from 4 mg/kg/day to 20 mg/kg/day of racemic norketotifen, or an isomer thereof, to dogs suffering from pruritic diseases.

The embodiments disclosed herein also provide pharmaceutical compositions, which comprise the compound norketotifen, its isomers, and salts, formulated together with one or more pharmaceutically acceptable carriers.

Pharmaceutical compositions for oral administration of solid dosage forms include capsules, granules, pills, powders and tablets. In solid dosage forms, the active compound may be mixed with one or more pharmaceutically acceptable excipients or carriers (such as for example sodium citrate, dicalcium phosphate), fillers or extenders (such as for example starch, lactose, sucrose, glucose, mannitol, silicic acid), binders (such as for example carboxymethylcellulose, alginates, gelatin, polyvinylpyrrolidone, sucrose, acacia), humectants (such as for example glycerol), solution retarding agents (such as for example paraffin), disintegrating agents (such as for example agar-agar, calcium carbonate, starch, alginic acid, silicates, sodium carbonate), absorption accelerators (such as for example quaternary ammonium compounds), wetting agents (such as for example cetyl alcohol, glycerol monostearate), absorbents (such as for example kaolin, bentonite clay), lubricating agents (such as for example talc, calcium stearate, magnesium stearate, polyethylene glycols, sodium lauryl sulfate), and/or other excipients, such as for example buffering agents.

Solid forms of capsules, granules, pills, and tablets can have coatings and/or shells (such as for example enteric coatings) known in the art. The compositions may also be designed to release the active ingredient(s) in a certain part of the gastrointestinal tract or in a controlled release, slow-release or in a delayed-release manner. The active compound(s) can also be microencapsulated with one or more of the above-mentioned excipients or other suitable excipients.

Liquid dosage forms for oral administration may be preferred administration forms to children suffering from pruritus. Such formulations include for example pharmaceutically acceptable solutions, emulsions, solutions, suspensions, syrups and elixirs. The liquid dosage form may also contain excipients known to those skilled in the art of drug formulations, such as for example diluents (such as for example water, other solvents and solubilizing agents, and mixtures thereof), and emulsifiers (such as for example ethanol, isopropyl alcohol, ethyl carbonate, ethyl acetate, benzyl alcohol, benzyl benzoate, propylene glycol, butylene glycol, dimethyl formamide, oils, oleic acid, glycerol, polyethylene glycols, sorbitan fatty esters, and mixtures thereof. The oral compositions may also include other excipients as known to those skilled in the art.

The compositions described here can also include other drugs with antipruritic activity, as for example a corticosteroid. Due to the antipruritic activity of norketotifen or the isomers thereof, a beneficial steroid-sparing effect will be possible when treating patients suffering from various types of pruritic disorders.

The invention is further illustrated by the following non-limiting examples.

Example 1

Inhibition of Histamine Release from Pro-Inflammatory Cells

Histamine is excessively released from granulocytes in patients with pruritic diseases. The inhibition of histamine release from human granulocytes (leukocytes; buffy coat) by test articles was studied. Leukocytes were obtained from blood from healthy human volunteers and release of histamine was induced by incubation (20 min/37° C.) of the buffy coats with the calcium ionophore A23187 (5 μM) in the presence or absence of a test article. Histamine was analyzed by enzyme-immune assays, using commercially available kits and a microplate reader (MRX, Dynatech). The test articles were evaluated, in duplicate, at five concentrations.

TABLE 1

Inhibition of histamine release from human granulocytes

| Test article | Inhibition of mediator release IC50 (μM) |
|---|---|
| Ketotifen | 91 |
| Norketotifen | 9.2 |

Norketotifen was approximately 10 times more potent than ketotifen as an inhibitor of histamine release from human inflammatory cells. Thus, norketotifen will potently decrease the concentration of histamine in inflamed tissues.

Example 2

Binding to Histamine H-1 Receptors

Affinities of the test compounds for peripheral human histamine H-1-receptors were assessed using receptor-binding assays. The specific binding of the radioactive ligand to the receptor was defined as the difference between total binding and nonspecific binding, determined in the presence of excess unlabeled ligand. Ki-values were determined according to the Cheng-Prusoff equation.

TABLE 2

Inhibition of human histamine H-1 Receptor (IC50)

|  | Human H-1 receptors IC50 (μM) |
|---|---|
| RS-NORKETOTIFEN (NORK) | 11 |
| S-NORKETOTIFEN (SNORK) | 23 |
| R-NORKETOTIFEN (RNORK) | 17 |
| KETOTIFEN | 2.3 |
| LORATADINE (Claritin ®*) | 1,500 |
| DESLORATADINE (Clarinex ®) | 16 |
| DIPHENHYDRAMINE (Benadryl ®) | 84 |

*Loratadine is the low-activity prodrug for desloratadine.

Norketotifen and the isomers thereof had high affinity for histamine H-1-receptors, similar to desloratadine and better than diphenhydramine.

The effects of the reference compounds (ketotifen, loratadine, desloratadine and diphenhydramine) verify the previously known receptor binding activities of these compounds, thereby validating the test methodology.

Example 3

Binding to Histamine H-4 Receptors

Affinities of the test compounds for peripheral human histamine H-4-receptors were assessed using receptor-binding assays. The specific binding of the radioactive ligand to the receptor was defined as the difference between total binding and nonspecific binding, determined in the presence of excess unlabeled ligand. [$^3$H]-histamine was used as the ligand in this study and the affinity values were determined according to the Cheng-Prusoff equation.

TABLE 3

Affinity for human histamine H-4 Receptor

|  | Human H-4 receptor affinity (Ki) |
|---|---|
| RS-NORKETOTIFEN (NORK) | 2.0E−0.6M |
| S-NORKETOTIFEN (SNORK) | 1.1E−06M |
| R-NORKETOTIFEN (RNORK) | 2.3E−06M |
| KETOTIFEN | 2.1E−05M |
| DESLORATADINE (Clarinex ®) | 1.6E−05M |
| DIPHENHYDRAMINE (Benadryl ®) | 1.1E−05M |

RS-, S- and R-norketotifen had affinity for the H-4 receptor, albeit lower affinity than the published corresponding values for super-potent and systemically active selective H-4—receptor active compounds, such as for example JNJ 7777120. It is not believed that RS-, S- and R-norketotifen will express systemic reversal of the activity of H-4 receptors unless the compounds appear in high concentrations at the receptor sites.

As known to those skilled in the art of pharmacology, high agonist concentrations are needed in these studies since the Cheng-Prusoff equation is resulting in erroneous values at low concentrations of agonists.

It is believed to be of therapeutic importance that norketotifen inhibits both histamine H-4 and histamine H-1 receptors since a potentiation of the antipruritic activity of histamine H-4 inhibition by histamine H-1 inhibition has been reported in the art, although histamine H-1 inhibition by itself has no antipruritic effects, as described in the art and as shown by the present results (Example 5; FIG. 1).

Example 4

Dermal Drug Accumulation after Oral Administration

Five male beagle dogs, weighing 11.2-13.9 kg (2-4 years old) were used in the study. All animals were administered gelatin capsules containing oral doses of the test article 8.0 mg/kg/day as a hydrogen fumarate salt, equal to 5.6 mg/kg/day of the free base. The animals were dosed once daily for four consecutive weeks followed by daily observations for an additional two-week washout period.

Multiple plasma samples and skin biopsies were taken from each dog on Day 1 and Day 28 of drug administration. The plasma and skin samplings were performed at pre-dose, and at 2, 6, 12 and 24 hours post-dose. Plasma and skin samples were also taken intermittently at predetermined intervals during the 28-days dosing period and up to the last day of the study, which was Day 42. Blood samples were taken from v. *Cephalica antebrachii*. Skin biopsies were taken from the area between the mid ventral to lateral abdominal areas, using a 6 mm (diameter) skin biopsy device (Acu-Punch®, Acuderm® Inc., Fort Lauderdale, Fla. 33309). Multiple plasma and biopsy samples were obtained from each of 4 or 5 dogs. Subcutaneous fat deposits were carefully trimmed from the skin samples and the skin samples were weighed. All plasma and skin samples were kept The plasma samples and skin biopsy samples were analyzed using LC/MS/MS methodology. All pharmacokinetic analyses were performed using Pharsight WinNonlin® Professional v5.2.1 software.

TABLE 4

Pharmacokinetic (PK) Parameters on Day 28 of Dosing.

| PK Parameter | S-NORK Plasma | S-NORK Skin | R-NORK Plasma | R-NORK Skin | RS-NORK Plasma | RS-NORK Skin |
|---|---|---|---|---|---|---|
| AUC$_{0-\infty}$ | 1627 | 25710 | 1658 | 20376 | 3286 | 54187 |
| t$_{1/2}$ (hr) | 10.9 | 162.7 | 7.7 | 157.0 | 10.5 | 167.6 |
| MRT (hr) | 11.3 | 159.0 | 14.1 | 159.1 | 12.8 | 169.3 |

AUC$_{0-\infty}$ = Area under the plasma concentration (or skin concentration) vs. time curves
t$_{1/2}$ = Plasma or skin half-life
MRT = Mean residence time
SNORK = S-norketotifen;
RNORK = R-norketotifen;
RS-NORK = total norketotifen Since norketotifen potently inhibits the release of histamine from pro-inflammatory cells (Example 1) and acts as an inverse agonist at the histamine H-4 receptors (Example 3), and since norketotifen is accumulated in the skin (Table 4), those skilled in the art will realize that the decreased availability of histamine together with the inhibitory activity at the histamine H-4 receptor site will act synergistically to reduce the G-protein-mediated signaling from dermal histamine H-4 receptors.

Example 5

Antipruritic Activity

Antipruritic effects were tested in vivo in CD-1 mice, females, 10-12 weeks, according to methods known in the art. The hair was clipped over the rostral part of the back at the interscapular level of the mice one day before the dosing. Before the testing, the mice were placed in individual clear plastic cages for at least one hour for acclimation. After fasting for 1.5 hours, the animals were dosed orally with the test article, dissolved in a vehicle consisting of 1% methylcellulose/water, 10 mL/kg body weight. Sixty minutes after the oral dosing, an intradermal injection of histamine (300 nmol in 20 μl phosphate buffered saline (PBS), pH 7.4) was administered. Immediately after the histamine injection, the bouts of scratches were counted for 40 min. Scratching induced by the histamine vehicle PBS served as control.

Norketotifen was tested in escalating doses and in a supramaximal dose of 100 mg/kg. JNJ7777120 and desloratadine were dosed orally with 20 mg/kg, which is within the murine dose ranges used for those compounds in the art. The vehicle for the reference compound JNJ7777120 was 20% hydroxypropyl-B-cyclodextrin in water. The vehicle for the reference compound desloratadine was the same as the vehicle for norketotifen (10 mL/kg of 1% methylcellulose in water). The test results are shown in FIG. 1. The numbers of pruritic bouts are expressed in percent of Vehicle (100% corresponds to 112 pruritic bouts). A test of the vehicle for JNJ7777120 demonstrated 112 bouts of pruritus (not shown in FIG. 1), which coincidentally was exactly the same number of bouts obtained for the methylcellulose vehicle. The reference compound desloratadine is a selective histamine H-1 inhibitor and the reference compound JNJ7777120 is a selective histamine H-4 inhibitor.

Norketotifen was dose-dependently inhibiting histamine-induced pruritus and a supramaximal dose (100 mg/kg) demonstrated complete inhibition. Scratches induced by the histamine-free vehicle PBS (not shown in FIG. 1) served as control (4±2 bouts of scratching; n=6)

It was concluded that norketotifen potently and dose-dependently decreased histamine-induced pruritus. The results from tests of a selective histamine-4 inhibitor and a selective histamine-1 inhibitors demonstrate that histamine H-4 inhibition, but not histamine H-1 inhibition blocks histamine—induced pruritus. The unexpectedly potent inhibition of pruritus by norketotifen may in part be due to potentiation caused by simultaneous expression of both histamine H-1 and histamine H-4 receptor inhibition by norketotifen.

Example 6

Exemplary Oral Dosage Formulation

Formulations for oral administration of norketotifen (such as for example tablets, capsules and syrups) have been developed.

TABLE 5

Tablet formulations

| Ingredient | Amount per tablet | Amount perbatch |
|---|---|---|
| Norketotifen | 20 mg | 200 g |
| Microcrystalline cellulose | 30 mg | 300 g |
| Lactose | 70 mg | 700 g |
| Calcium stearate | 2 mg | 20 g |
| FD&C Blue #1 Lake | 0.03 mg | 300 mg |

The active ingredient is blended with the lactose and cellulose until a uniform blend is formed. The blue lake is added and further blended. Finally, the calcium stearate is blended in, and the resulting mixture is compressed into tablets using for example a 9/32-inch (7 mm) shallow concave punch. Tablets of other strengths may be prepared by altering the ratio of active ingredient to the excipients or to the final weight of the tablet.

Those skilled in the art realize that oral formulations can be in the form of, for example, a tablet, a capsule, a dog-treat, a cat-treat, a syrup or another form of liquid formulation.

As used herein, the terms "pharmaceutically acceptable salts" or "a pharmaceutically acceptable salt thereof" refer to norketotifen salts, which have been prepared from pharmaceutically acceptable non-toxic acids. Exemplary pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. The hydrochloride salt and the hydrogen fumarate salt are particularly preferred.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. As used herein, the term mammal includes humans, dogs, and cats. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of treating a mammal with selective inverse histamine H-1 agonists, and wherein the histamine H-4 receptor-related pruritus is associated with a dermal disorder selected from autoimmune dermatitis, contact dermatitis, dermal *scleroderma*, folliculitis, an insect bite, melanoma, parasites, scabies, sunburn, warts, xerosis, moles, and idiopathic pruritus.

2. The method of claim 1, wherein the mammal is a human.

3. The method of claim 2, wherein the therapeutically effective amount of RS-norketotifen or a pharmaceutically acceptable salt thereof is 2 to 500 mg/day.

4. The method of claim 1, wherein the mammal is a dog.

5. The method of claim 4, wherein the therapeutically effective amount of RS-norketotifen or a pharmaceutically acceptable salt thereof is 2 mg/kg/day to 28 mg/kg/day.

6. The method of claim 1, wherein the histamine H-4 receptor-related pruritus is associated with adverse effects of a drug.

* * * * *

UNITED STATES PATENT AND TRADEMARK OFFICE
CERTIFICATE OF CORRECTION

PATENT NO. : 9,138,431 B2  
APPLICATION NO. : 13/960114  
DATED : September 22, 2015  
INVENTOR(S) : A. K. Gunnar Aberg et al.

Page 1 of 2

It is certified that error appears in the above-identified patent and that said Letters Patent is hereby corrected as shown below:

On the title page, item (56), in column 2, under "Other Publications", line 7, delete "Vererinary" and insert -- Veterinary --, therefor.

On the title page, item (56), in column 2, under "Other Publications", line 13, delete "Uto," and insert -- Ito, --, therefor.

On the title page, item (56), in column 2, under "Other Publications", line 14, delete "Nery" and insert -- Nerv --, therefor.

On the page 2, item (56), in column 1, under "Other Publications", lines 28-30, below "(2001).", delete "Ito, C.; "Histamine H3-receptor Inverse Agonists as Novel Antipsychotics"; Cent Nery Syst Agents Md Chem.; PubMed--NCBI; 2009; abstract only; printed Dec. 14, 2012; 1 page.".

On the page 2, in column 1, under "Other Publications", line 65, delete "Diabetees" and insert -- Diabetes --, therefor.

On the page 2, in column 2, under "Other Publications", line 1, delete "Determatitis:" and insert -- Dermatitis: --, therefor.

On the page 2, in column 2, under "Other Publications", line 15, delete "Robbach" and insert -- Rossbach --, therefor.

On the page 2, in column 2, under "Other Publications", line 16, delete "Imflammation" and insert -- Inflammation --, therefor.

On the page 2, in column 2, under "Other Publications", line 18, delete "Robbach" and insert -- Rossbach --, therefor.

On the page 2, in column 2, under "Other Publications", line 27, delete "Histaminen" and insert -- Histamine --, therefor.

On the page 2, in column 2, under "Other Publications", line 30, delete "Statistocs" and insert -- Statistics --, therefor.

Signed and Sealed this  
Fifth Day of April, 2016

Michelle K. Lee  
*Director of the United States Patent and Trademark Office*

CERTIFICATE OF CORRECTION (continued)
U.S. Pat. No. 9,138,431 B2

On the page 2, in column 2, under "Other Publications", line 42, delete "Untersuchunger" and insert -- Untersuchungen --, therefor.

On the page 2, in column 2, under "Other Publications", line 44, delete "thiophenenSynthetical" and insert -- thiophenen Synthetical --, therefor.

On the page 2, in column 2, under "Other Publications", line 58, delete "Allgergy" and insert -- Allergy --, therefor.

On the page 2, in column 2, under "Other Publications", line 60, delete "Pzotifen" and insert -- Pizotifen --, therefor.

On the page 3, in column 1, under "Other Publications", line 5, delete "Robbach" and insert -- Rossbach --, therefor.

In the specification,

In column 10, line 32, delete "pathothenic," and insert -- pantothenic, --, therefor.

In the claims,

In column 11, lines 8-14, in claim 1, delete "1. A method of treating a mammal with selective inverse histamine H-1 agonists, and wherein the histamine H-4 receptor-related pruritus is associated with a dermal disorder selected from autoimmune dermatitis, contact dermatitis, dermal scleroderma, folliculitis, an insect bite, melanoma, parasites, scabies, sunburn, warts, xerosis, moles, and idiopathic pruritus." and insert -- 1. A method of treating a mammal in need of treatment for histamine H-4 receptor-related pruritus, comprising orally administering to the mammal in need thereof a therapeutically effective amount of RS-norketotifen or a pharmaceutically acceptable salt thereof, thereby reducing the desire to scratch in the mammal, wherein the histamine H-4 receptor-related pruritus is resistant to treatment with selective inverse histamine H-1 agonists, and wherein the histamine H-4 receptor-related pruritus is associated with a dermal disorder selected from autoimmune dermatitis, contact dermatitis, dermal scleroderma, folliculitis, an insect bite, melanoma, parasites, scabies, sunburn, warts, xerosis, moles, and idiopathic pruritus. --, therefor.